US008070740B2

(12) United States Patent
Govil et al.

(10) Patent No.: US 8,070,740 B2
(45) Date of Patent: Dec. 6, 2011

(54) PROCESSES AND SYSTEMS FOR HYDRATING AND SEEDING MEDICAL IMPLANTS WITH BIOLOGICAL COMPONENTS

(75) Inventors: Amit Govil, San Diego, CA (US); Christian Gamboa, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 452 days.

(21) Appl. No.: 12/130,920

(22) Filed: May 30, 2008

(65) Prior Publication Data
US 2009/0137042 A1    May 28, 2009

Related U.S. Application Data

(60) Provisional application No. 60/932,479, filed on May 30, 2007.

(51) Int. Cl.
*A61M 5/00*    (2006.01)
*A61K 31/74*   (2006.01)
*A61F 2/28*    (2006.01)
(52) U.S. Cl. ............... 604/416; 424/78.02; 623/16.11; 623/23.61
(58) Field of Classification Search .................. None
See application file for complete search history.

(56) References Cited

U.S. PATENT DOCUMENTS

| | | | |
|---|---|---|---|
| 6,349,850 B1 | 2/2002 | Cheikh | 222/1 |
| 6,648,133 B1 | 11/2003 | Blaschke et al. | 206/221 |
| 6,830,149 B2 | 12/2004 | Merboth | 206/438 |
| 7,017,763 B2 | 3/2006 | Kelley | 215/383 |
| 7,172,071 B2 | 2/2007 | Hawkins | 206/438 |
| 7,198,150 B1 | 4/2007 | Blaschke et al. | 206/221 |
| 2002/0165611 A1 | 11/2002 | Enzerink et al. | 623/13.11 |
| 2003/0190596 A1 | 10/2003 | Brandt et al. | 435/1.1 |
| 2005/0167309 A1 | 8/2005 | Iwatschenko | 206/438 |
| 2006/0108239 A1 | 5/2006 | Iwatschenko | 206/63.5 |
| 2006/0154231 A1 | 7/2006 | Brandt et al. | 435/1.1 |
| 2007/0016215 A1* | 1/2007 | Wilander et al. | 606/93 |
| 2007/0118068 A1 | 5/2007 | Hawkins | 604/19 |

OTHER PUBLICATIONS

Basic Science and Pathology, The Effects of Freeze Drying and Rehydration on Cancellous Bone, Ernest U. Conrad, M.D., Donald P. Ericksen, B.S., Allan F. Tencer, Ph.D., Douglas M. Strong, Ph.D., and Allan P. MacKenzie, Ph.D., 1993 Clinical Orthopaedics and Related Research No. 290, pp. 279-284.
Synthesis of antibiotic-loaded interporous hydroxyapatite blocks by vacuum method and in vitro drug release testing, Mansho Itokazu, Wenyi Yang, Takaaki Aoki, Akira Ohara, Naoki Kato, Biomaterials 19 (1998), pp. 817-819, 1998 Published by Elsevier Science Ltd.
Local drug delivery system using ceramics: vacuum method for impregnating a chemotherapeutic agent into a porous hydroxyapatite block, M. Itokazu, M. Esaki, K. Yamamoto, T. Tanemori, T. Kaisi, Department of Orthopaedic Surgery, Journal of Materials Science: Materials in Medicine 10 (1999), pp. 249-252.
Use of commercial porous ceramic particles for sustained drug delivery, R.S. Byrne, P. B. Deasy, Department of Pharmaceutics and Pharmaceutical Technology, School of Pharmacy, University of Dublin, Trinity College, Dublin, Ireland, International Journal of Pharmaceutics 246 (2002), pp. 61-73.
Effects of Filtration Seeding on Cell Density, Spatial Distribution, and Proliferation in nonwoven Fibrous Matrices, Yan Li, Teng Ma, Douglas A. Kniss, Larry C. Lasky, and Shang-Tian Yang, Department of Chemical Engineering, Laboratory of Perinatal Research, Department of Obstetrics and Gynecology, and Departments of Pathology and Internal Medicine, The Ohio State University, Columbus, Ohio, Biotechnol. Prog. 2001, 17, pp. 935-944.
Application of low-pressure system to sustain in vivo bone formation in osteoblast/porous hydroxyapatite composite, Jian Dong, Toshimasa Uemura, Hiroko Kojima, Masanori Ikuchi, Junzo Tanaka, Tetsuya Tateishi, Materials Science and Engineering C 17 (2001), pp. 37-43.
The Navy Tissue Bank, Sarah C. McGinniss, The American Journal of Nursing, vol. 59, No. 5 (May 1959), pp. 666-6669.

* cited by examiner

*Primary Examiner* — Elizabeth C Kemmerer
*Assistant Examiner* — Xiaozhen Xie
(74) *Attorney, Agent, or Firm* — Michael R. Shevlin; Alphatec Spine, Inc.

(57) ABSTRACT

Methods and systems for providing an improved apparatus and packaging system to more expeditiously hydrate or reconstitute medical grafts and to effectively and uniformly seed the medical grafts with biological components and cultured cells. The systems generally comprise a container comprising entry port, at least one substrate cavity, and top, side and bottom walls defining an inner surface. The entry port is configured to receive the biological solution. The cavity is in communication with the entry port and includes the porous substrate maintained under negative pressure. The container volume is substantially the same as a volume of the porous substrate. The side and bottom walls are configured to promote a laminar flow of the biological solution received through the entry port.

15 Claims, 5 Drawing Sheets

PROCESSES AND SYSTEMS FOR HYDRATING AND SEEDING MEDICAL IMPLANTS WITH BIOLOGICAL COMPONENTS

CROSS-REFERENCE TO RELATED APPLICATIONS

This application claims priority pursuant to 35 U.S.C. §119 (e) to U.S. provisional application Ser. No. 60/932,479, filed May 30, 2007, which is hereby incorporated by reference in its entirety.

FIELD OF THE INVENTION

The present invention relates generally to medical implants and more particularly to methods and systems for hydrating and seeding medical implants with biological components.

BACKGROUND

Bone grafting refers to a wide variety of medical and dental surgical procedures by which the formation of new bone in a patient is augmented or stimulated. Bone grafting is used in many types of orthopedic procedures to treat bone fractures or loss, to repair injured bone that has not healed, and to fuse together joints to prevent movement. With particular reference to the spine, grafts have been used to stabilize the spine and to prevent movement by selected vertebral segments, which may be a significant cause of pain in some patients. Grafts have also been used to correct or stop the progress of spinal deformity, such as scoliosis, and to provide structural support for fractures of the spine.

Suitable grafts may be harvested from bones in the patient's own body (autografts), from bones in members of the same species (allograft), and from bones in members of other animal species (xenograft). Alternatively, bone grafts may be created from a wide variety of natural and/or synthetic materials, such as collagen, polymers, hydroxyapatite, calcium sulfate, ceramics, and bioresorbable polymers, among many others. It is understood that bone grafts may include those which have a predetermined shaped or which are comprised of smaller particles that may be formed into a desired shape at the time of implantation.

Regardless of the source, bone grafts must be adequately preserved for later implantation in a surgical setting. One common practice is to dehydrate the grafts by freeze-drying. This not only extends the shelf-life of the bone grafts, it also inhibits bacterial growth within the graft. Before implanting the graft into a recipient, however, the graft must be reconstituted or rehydrated with a suitable liquid. In order to implant a graft into a recipient, the graft must be reconstituted or hydrated with a suitable liquid. This may be done by immersing the bone graft in the liquid. The problem with this approach, however, is that infusion of the liquid through the pores of the graft is typically unacceptably slow for a surgical environment and does not ensure thorough and complete infusion of the liquid throughout the graft. Moreover, this approach increases the likelihood of exposing the graft to environmental pathogens.

Another significant challenge in preparing grafts for implantation is the uniform loading or seeding of grafts with desired biological components and cultured cells. Developing functional tissue equivalents requires the effective and uniform seeding of biological components and cells into natural or synthetic matrices and allowing them to expand and develop into the tissue-like structure from the seeded cells. Thus, the ability to efficiently and uniformly seed biological components and cells into three-dimensional scaffolds remains a significant aspect in tissue engineering.

SUMMARY

Methods and systems are disclosed herein for providing an improved apparatus and packaging system to more expeditiously reconstitute and hydrate medical grafts and to effectively and uniformly seed the medical grafts with biological components and cultured cells.

In one preferred embodiment, a system for loading a biological solution into a porous substrate is provided. The system generally comprises a container comprising an entry port, at least one substrate cavity, and top, side and bottom walls defining an inner surface of the container. The entry port is configured to receive the biological solution. The cavity is in communication with the entry port and includes the porous substrate maintained under negative pressure. The container volume is substantially the same as a volume of the porous substrate. The side and bottom walls are configured to promote a laminar flow of the biological solution received through the entry port.

In accordance with one aspect of the preferred embodiment, the side and bottom walls of the container converge into curved surfaces having radii of curvature greater than zero.

In accordance with another aspect of the preferred embodiment, the system further comprises a needle cavity disposed in the container and adjacent the entry port and the at least one substrate cavity. The container may optionally comprise a plurality of substrate cavities in communication with the needle cavity. A septum may be coupled to the entry port and disposed externally of the container.

In accordance with yet another aspect of the preferred embodiment, the container volume is no greater than 125%, preferably no greater than 110%, and most preferably no greater than 105% of the volume of the porous substrate.

In accordance with a further aspect of the preferred embodiment, the system further comprises one or more supporting members configured to elevate and support the at least one cavity in a substantially stable position. The bottom wall may be angled down from the entry port. This configuration will ensure that the biological solution does not pool in the area surrounding the entry port and is distributed along the bottom of the porous substrate. The bottom wall may be angled at about 5o to about 25o downward from the port.

In accordance with yet a further aspect of the preferred embodiment, the container further comprises a lip surrounding a periphery of the container. The lip may provide a surface for handling the container by the surgeon. The lip may also provide a surface onto which the top wall of the container is hermetically sealed around the periphery of the container. In addition, a support rib may also be disposed peripherally of the cavity to maintain the structural integrity of the container.

In another preferred embodiment, a container for storing a porous substrate is provided. The container comprises an internal cavity maintained under negative pressure. The internal cavity comprises a first receiving chamber configured to receive a biological solution and a second storage chamber configured to store the porous substrate. A plurality of channels couples the first receiving chamber and the second storage chamber. The plurality of channels is configured to disperse the distribution of the biological solution along a longitudinal length of the porous substrate at substantially the same time once the first receiving chamber receives the biological solution.

In accordance with one aspect of the preferred embodiment, the container further comprises a seal adjacent a periphery of the container so as to reduce a volume of air space within the container.

In accordance with another aspect of the preferred embodiment, the container further comprises a septum coupled to the first receiving chamber and disposed externally of the internal cavity. The septum may a self-sealing septum and is thus resealable after puncture with a needle syringe to maintain the negative pressure in the internal cavity.

In a further embodiment, a method for seeding biological components and cultured cells into a dehydrated porous substrate is provided. The method comprises providing the dehydrated porous substrate in a container under negative pressure, wherein a container volume is substantially the same as a porous substrate volume. Next, a biological solution is introduced to the dehydrated porous substrate in a volume that does not exceed the porous substrate volume. The biological solution may comprise any one or a combination of biological components and cultured cells.

In accordance with one aspect of the preferred embodiment, the method further comprises the step of maintaining the negative pressure in the container for a time sufficient to allow the biological solution to permeate through the porous substrate.

In accordance with a further aspect of the preferred embodiment, the step of introducing the biological solution to the dehydrated porous substrate is performed using a needle syringe.

Other objects, features and advantages of the present invention will become apparent to those skilled in the art from the following detailed description.

BRIEF DESCRIPTION OF THE DRAWINGS

Like numerals refer to like parts throughout the several views of the drawings.

DETAILED DESCRIPTION OF EMBODIMENTS OF THE INVENTION

The present disclosure is directed to methods and systems for expeditiously reconstituting and hydrating medical grafts and for uniformly seeding medical grafts with biological components and cultured cells. The methods and systems disclosed herein are particularly suited for surgical environments where the ability to quickly prepare grafts for implantation in a patient is desired.

Figure 1A:
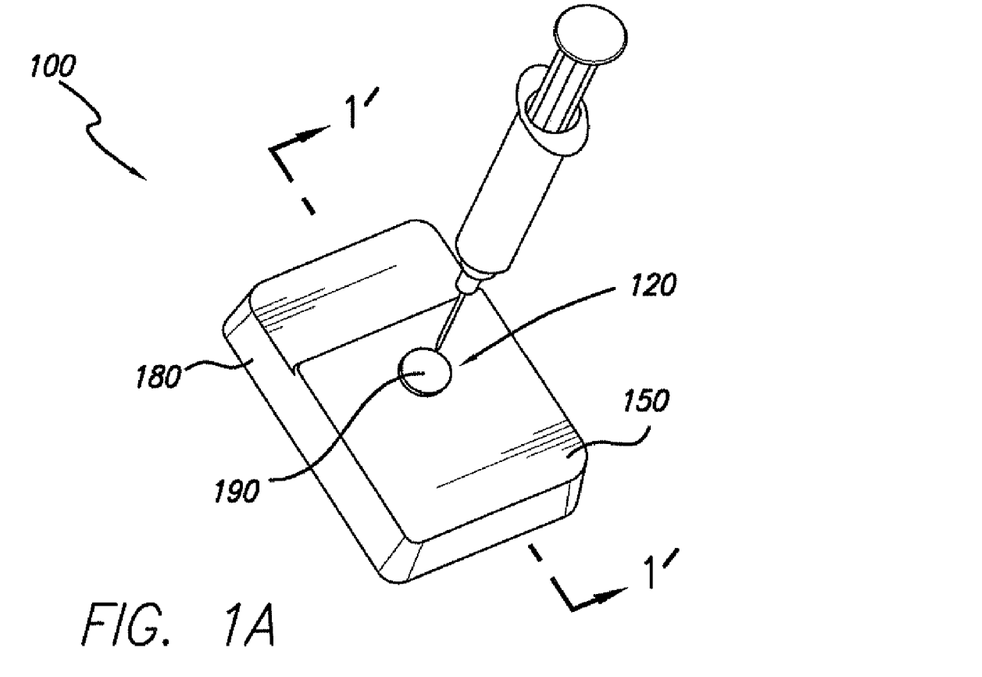
FIG. 1A is a top perspective view of an embodiment of a medical implant container.
Figure 1B:
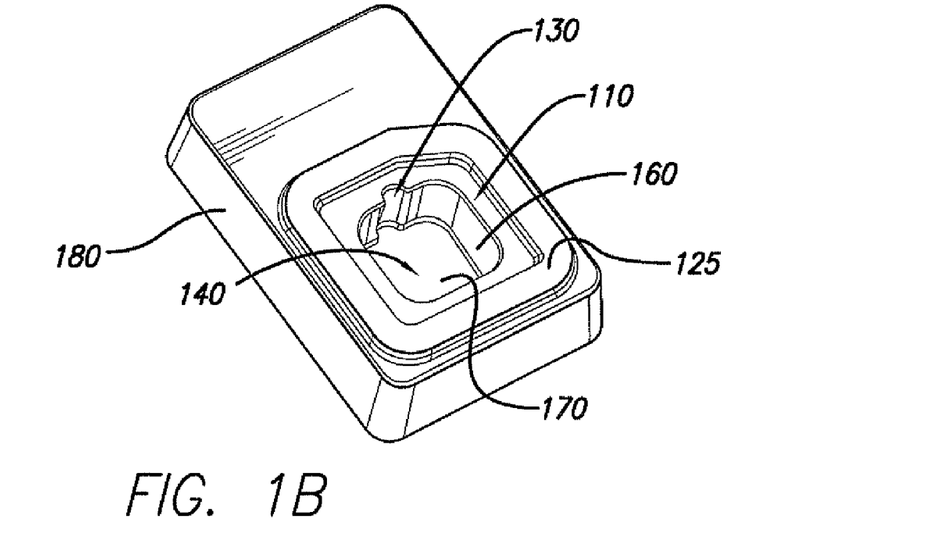
FIG. 1B is a top perspective view of the medical implant container of FIG. 1 without the lid.
Figure 1C:
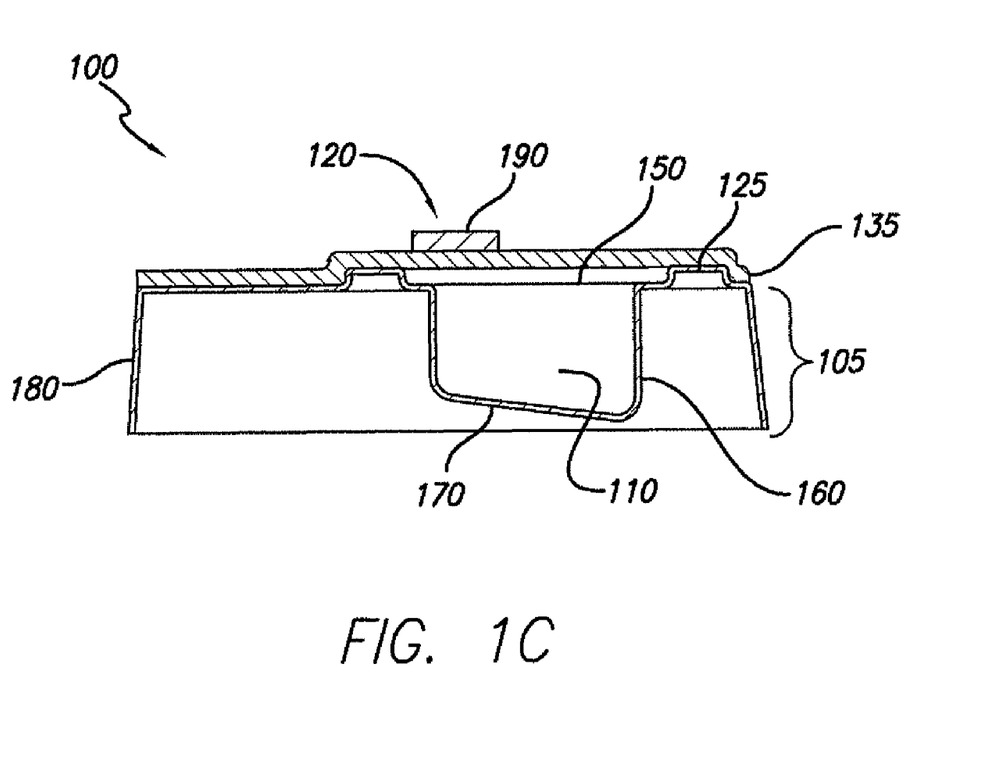
FIG. 1C is a cross-sectional view of the medical implant container of FIG. 1A taken along the 1'-1' axis

FIGS. 1A-C depict various views of an embodiment of a medical implant system 100 that may be used in connection with the systems and methods disclosed herein. As shown in FIGS. 1A-C, the medical implant system 100 comprises container 110 that includes an entry port 120, a needle cavity 130 and a graft cavity 140 containing a medical implant, such as a dehydrated bone graft (not shown). As shown in FIG. 1A, a needle syringe may be inserted through the entry port 120 to deliver liquids, biological components, and/or cells into the needle cavity 130 and to the graft that is stored in the graft cavity 140 of the container 110. The needle cavity 130 is disposed adjacent the graft cavity 140 to receive the needle syringe and the liquids, biological components and/or cell.

It is desirable to maintain the entire container 110 under negative pressure and, more preferably, under substantially vacuum. This is because medical implants, such as bone grafts, are commonly dehydrated and freeze-dried for storage prior to use or implantation. Freeze-drying involves a freezing process under negative pressure that results in a graft having low residual moisture. One advantage of this process is that it allows for storage of bone grafts and other biological material at room temperature. It also provides for increased the shelf-life with reduced biochemical changes to the bone graft. Freeze-dried grafts thus offer the advantage of providing easy and economical storage prior to use.

The bone graft is typically rehydrated or reconstituted with a saline solution prior to implantation in a patient or recipient. Rehydration of freeze-dried bone grafts typically involves soaking the grafts in the saline solution until the grafts reach the desired level of hydration. Depending on the size of the graft, among other factors, rehydration and reconstitution of a bone graft may take anywhere from one hour to a few days. Although it is desirable to achieve uniform penetration of the solution and homogenous rehydration of bone grafts, it is generally difficult to achieve these goals in the short period of time typically demanded in surgical environments.

The medical implant containers disclosed and described herein provide a means by which bone grafts, which have been freeze-dried or otherwise dehydrated, may be expeditiously and uniformly hydrated and reconstituted prior to implantation. Because the medical implant containers substantially maintain the negative pressure during the hydration/reconstitution of the graft, the time for hydration or reconstitution is substantially reduced. The penetration of solution into the implant is enhanced by the vacuum induced suction effect. The negative pressure produces a pressure differential that pushes the solution into the interstice or pores of the implant. Once the solution is distributed into the pores, it may be further distributed throughout the implant via capillary action.

In FIGS. 1A-C, since the entire container 110 is maintained under negative pressure or vacuum, it is desirable to reduce the internal volume of the container 110 to the extent necessary to house the bone graft. This is because it is generally more difficult to maintain negative pressure or a vacuum for larger volumes of space. In a preferred embodiment, the volume of the container is substantially the same as the volume of the graft. In accordance with one aspect this preferred embodiment, the volume of the container is no greater than approximately 125%, preferably no greater than approximately 110%, and more preferably no greater than 105%, of the volume of the graft. In accordance with another aspect of this preferred embodiment, the volume of the container is equal to the volume of the graft. As shown in FIGS. 1A-C, the interior volume of the container 110 is bounded by top 150, side 160 and bottom 170 walls. A septum 190 is coupled to the entry port 120 and disposed externally of the container 110 so as to reduce an internal volume of the container 110 required to accommodate the septum.

Figure 4A:
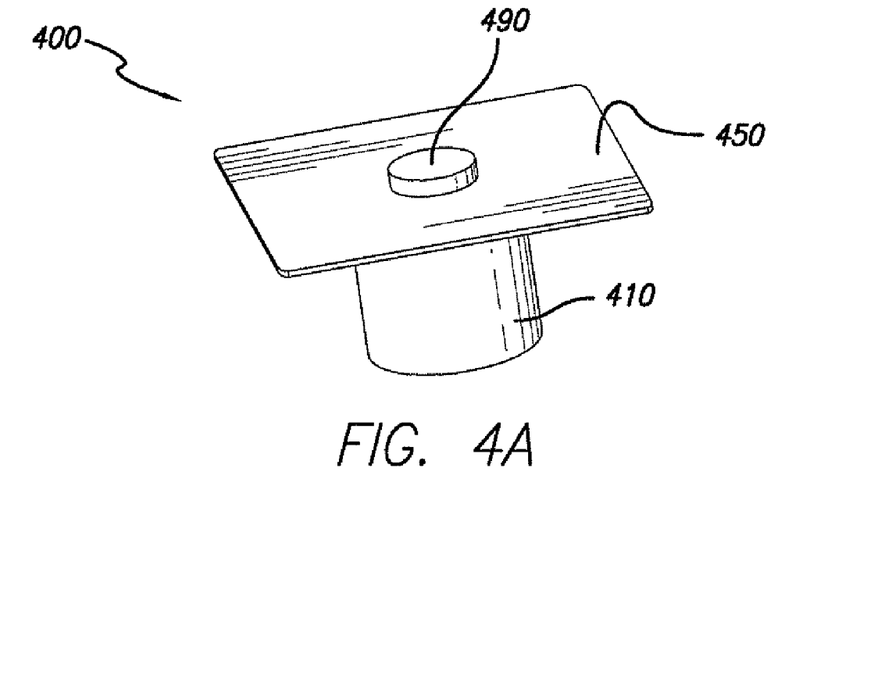
FIG. 4A is a top perspective view of yet a further embodiment of the medical implant container.
Figure 4B:
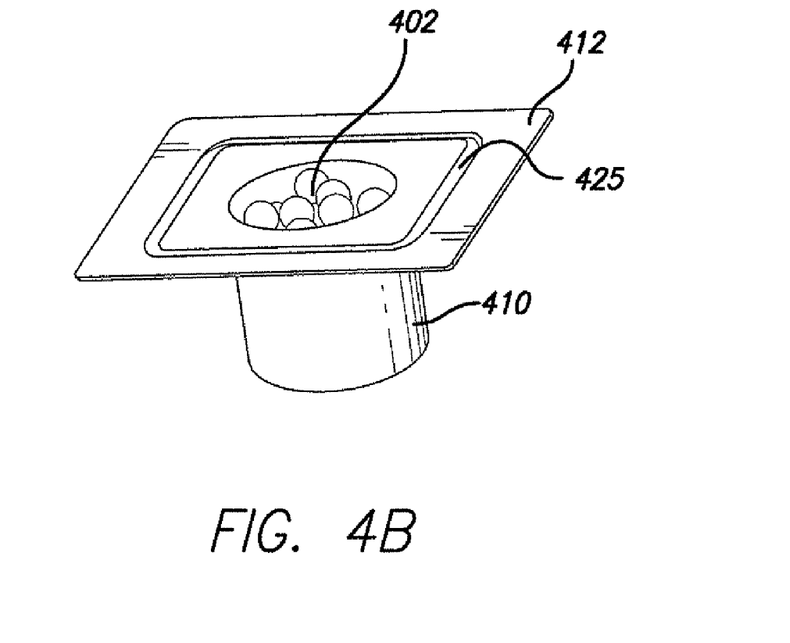
FIG. 4B is a top perspective view of the medical implant container of FIG. 4A without the lid.

Other embodiments of the medical implant containers may be similarly designed to reduce the internal volume that is maintained under negative pressure. For example, FIGS. 4A-B depicts a medical implant container 400 comprising bone graft chips 402 contained within a graft cavity 410. A lid 450 is hermetically sealed to the peripheral lip 412 of the graft cavity 410 by a heat weld 425. As can be seen in FIGS. 4A-B, the bone graft chips 402 fill the graft cavity 410 to near capacity such that the volume of the graft cavity 410 is substantially the same as the volume of the bone graft chips 402. A septum 490 is disposed externally of the graft cavity 410. Preferably, the septum is self-sealing after puncture with a needle syringe delivering the hydrating solution to the graft chips 402 so as to sustain the negative pressure/vacuum inside the graft cavity 410.

Referring back to FIGS. 1A-C, the medical implant system 100 further comprises support members 180 to support the container 110 in a substantially stable and upright position. This will permit the surgeon to place the system 100 on a flat surface and simply insert a needle syringe into the entry port 120 with a single hand without having to support the system 100 with the other hand in the desired upright position. Although FIGS. 1A-C shows the support members 180 as a single peripheral wall that surrounds the container 110, it is understood that the structure of the support members 180 is not so limited and may include other structures capable of stabilizing the container 110 in a sufficiently stable position to permit the surgeon to perform the injection step into the entry port 120.

The system 100 is shown to generally comprise a bottom portion 105 and a lid portion 135. The bottom portion 105 and the lid portion 135 may be hermetically-sealed by welding the two portions together so that a negative pressure may be maintained inside the container 110. It is preferable to position the weld as close to the periphery of the container 110 so as to further reduce the amount of dead airspace that may remain between the bottom portion 105 and the lid portion 135. The resulting weld 125 may surround the entire periphery of container 110. Although the system 100 depicted in FIGS. 1A-C is shown as a two-part structure comprising a bottom portion 105 and a lid 135, it is understood that the container may be constructed as an integral structure, such as an elastic vacuum package.

In addition to providing a means for expeditiously and uniformly hydrating or reconstituting bone grafts, the system 100 further provides a means for distributing biological components and/or for seeding cells into the pores of the grafts. Biological components and cells may be delivered to the grafts in solution via needle syringe having the appropriate gauge so as to ensure against structural or cellular damage as they are passed through the needle syringe.

Generally, there are three ways in which a graft can help repair a bone defect. The first is called osteogenesis, the formation of new bone by the cells contained within the graft. The second is osteoinduction, a chemical process in which molecules contained within the graft, such as bone morphogenic proteins, convert the patient's cells into cells that are capable of forming bone. The third is osteoconduction, a physical effect by which the graft forms a scaffold onto which cells in the recipient are able to colonize and form new bone. Thus, the methods and systems disclosed herein provide means by which grafts may be prepared to include biological components and cells to help repair a bone defect in the recipient.

The interior surface of the container 110 is configured to help preserve the integrity of the biological components and the cells during delivery to the bone graft. Particularly, the needle port 130 and the side 160 and bottom 170 walls are configured to promote a laminar flow of the biological solution received through the entry port. A laminar flow may be characterized either as smooth or non-turbulent fluid flow. It is preferable to promote a laminar flow, and therefore reduce a turbulent flow, of the biological solution in the container 110 so as to preserve the structural and cellular integrity of the biological components and cells contained in the solution. A turbulent flow may, for example, cause the cells to become lysed and clump together. Eliminating, or at least reducing, sharp edges, corners or angles within the container 110 which the biological solution may come into contact with in the container may help promote a laminar flow of the solution. It is noted that because the liquid is expelled into the needle cavity and towards the bottom surface 170 of the container 110, the configuration of the top wall or lid portion 105 of the container 110 or where the side walls 160 meet the lid portion 105 of the container 110 are not critical and therefore do not necessarily need to be curved.

As can be seen in FIGS. 1B-C, the side 160 and bottom 170 walls of the container 110 converge together as curved surfaces having radii of curvature greater than zero. Moreover, the internal surface of the needle cavity 130 is also provided as a curved surface having a radius of curvature greater than zero. Additionally, as shown in FIG. 1C, the bottom wall 170 is angled downward from the entry port 120 and the needle cavity 130 so as to ensure that the biological solution flows across and is distributed along a bottom length of the graft. This not only ensures the uniform distribution of the solution throughout the graft, it also prevents the pooling and waste of the solution in the needle cavity 130. Thus, embodiments of the medical implant container further provide for substantially precise dosing of a quantity of biological components or cells to be introduced.

Figure 2A:
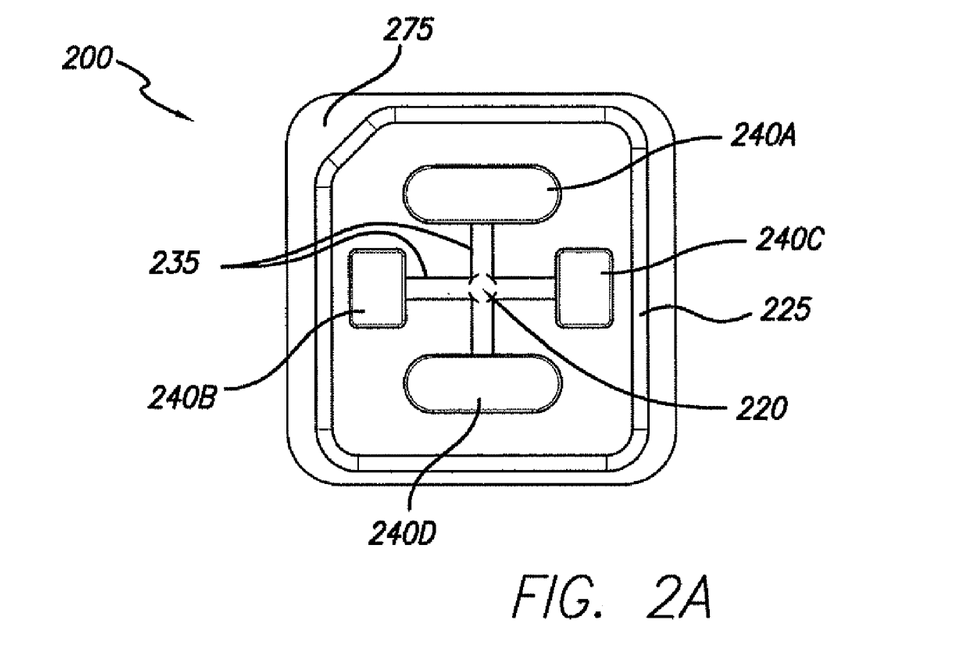
FIG. 2A is a front plan view of another embodiment of the medical implant container.
Figure 2B:
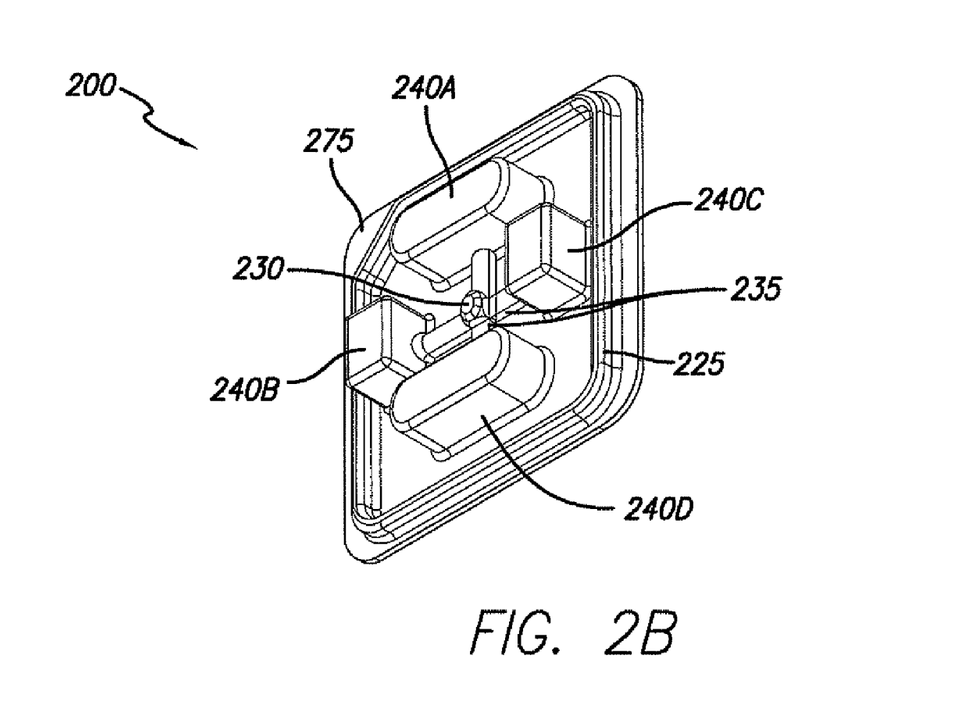
FIG. 2B is a rear perspective view of the medical implant container of FIG. 2A.

Alternate embodiments may provide an efficient means to hydrate or reconstitute more than a single bone graft at the same time. FIGS. 2A-B show an embodiment of the medical graft container 200 comprising a single entry port 220 and a corresponding needle cavity 230 and a plurality of graft cavities 240A, 240B, 240C, and 240D coupled to and in fluid communication with the needle cavity 230 via channels 235. Once the grafts are loaded into the graft cavities 240A, 240B, 240C, and 240D, a gas communication is applied to the container so as to evacuate air remaining in the graft cavities. The container 200 is then hermetically-sealed by a weld 225.

Developing functional tissue equivalents requires the effective and uniform seeding of biological components and cells into natural or synthetic matrices and allowing them to expand and develop into the tissue-like structure from the seeded cells. Thus, the ability to efficiently and uniformly seed biological components and cells into three-dimensional scaffolds remains highly desirable.

Figure 3:
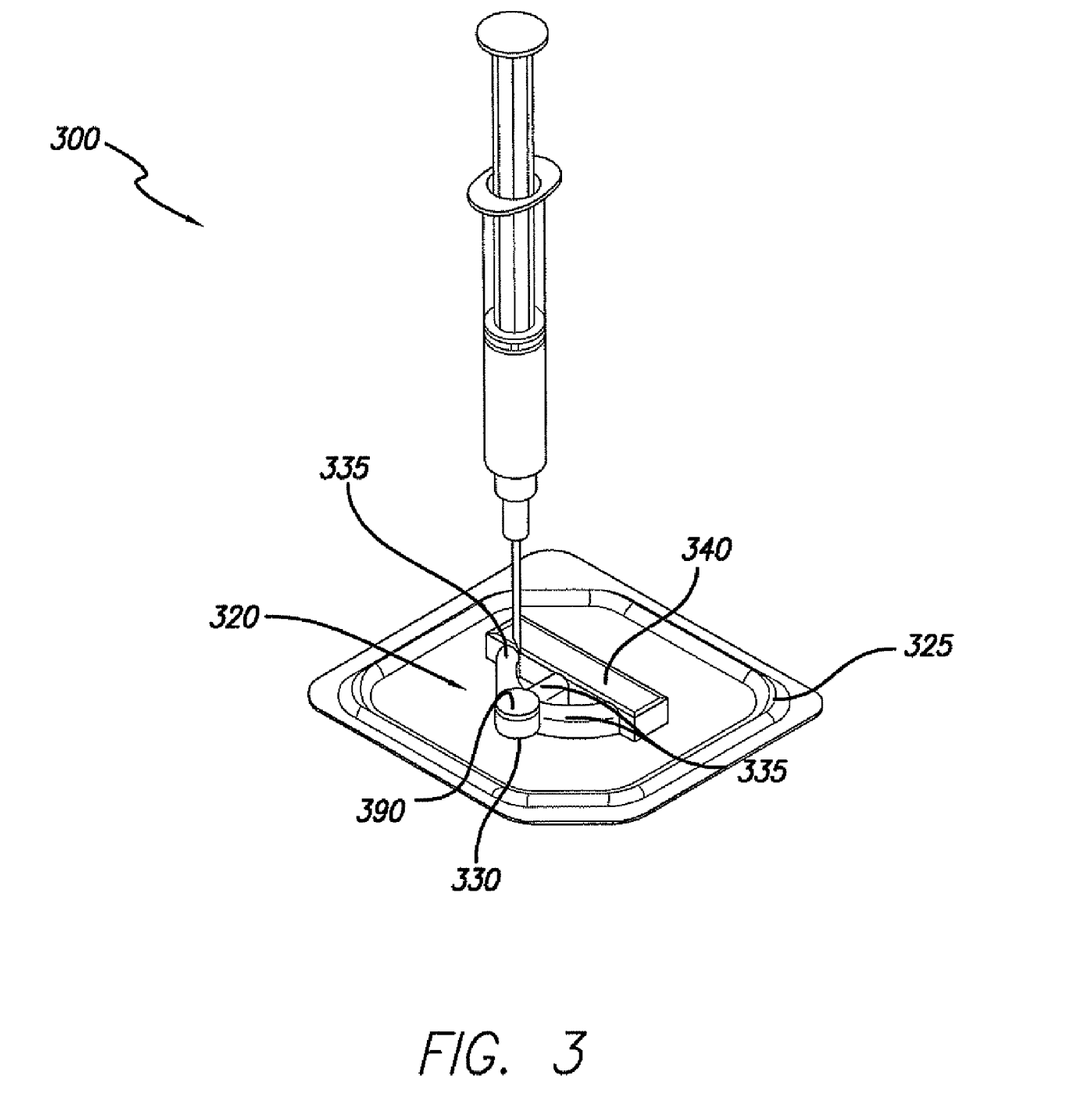
FIG. 3 is a top perspective view of a further embodiment of the medical implant container alongside a needle syringe.

FIG. 3 depicts yet another embodiment of the medical graft container 300 alongside a needle syringe. The container 300 is designed to disperse the distribution of desired biological components and cultured cells by providing a plurality of delivery channels 335 along a length of the graft cavity 340. The graft cavity 340 is preferably molded to the precise dimensions and shape of the dehydrated bone graft. The biological components and cultured cells may be delivered via needle syringe through entry port 320 and into the needle cavity 330. A negative pressure or vacuum is maintained in the needle cavity 330, the delivery channels 335 and graft cavity 340. A septum 390 may optionally be coupled to the entry port 320 to maintain the negative pressure or vacuum after puncture with the needle syringe. The container 300 may be hermetically sealed by a weld 325 peripherally of the needle cavity 330, delivery channels 335 and graft cavity 340.

The aqueous compositions used herein to hydrate or reconstitute the bone grafts prior to implantation may be solutions, emulsions, micro-emulsions, suspensions or combinations thereof. Materials that function as emulsifiers or suspension aids may also be present in such aqueous compositions. Non-limiting examples of such emulsifiers or suspension aids include cell growth mediums, serums, differentiation mediums, nutritional mediums, monoglycerides, esters of monoglycerides, diglycerides, esters of diglycerides, polyglycerol esters of fatty acids, propylene glycol esters of fatty acids, sorbitan stearates, stearoyl lactates, lecithins, phospholipids, glycolipids, cellulose esters, gellan, pectin, xanthan, rhamsam and gum arabic.

In some embodiments, the aqueous compositions may further contain water-miscible biocompatible solvents or solvent mixtures. The biocompatible solvents are preferably organic liquids in which the grafts may be at least partly soluble at mammalian body temperatures and is substantially non-toxic in the quantities used. By way of an example, suitable water-miscible biocompatible solvents include ethanol, acetone, and dimethylsulfoxide.

Biological components used in connection with the medical implants disclosed herein may include any agent that produces a biological, therapeutic or pharmacological result in a human. Exemplary biological components include, for example, bone morphogenic proteins; angiogenic factors; growth factors; hormones; anticoagulants, such as heparin and chondroitin sulphate; fibrinolytics, such as tPA; amino acids; peptides and proteins, including enzymes such as streptokinase, urokinase and elastase; steroidal and non-steroidal anti-inflammatory agents, such as hydrocortisone, dexamethasone, prednisolone, methylprednisolone, promethazine, aspirin, ibuprofen, indomethacin, ketorolac, meclofenamate, tolmetin; calcium channel blockers, such as diltiazem, nifedipine, verapamil; antioxidants such as ascorbic acid, carotenes and alpha-tocopherol, allopurinol, trimetazidine; antibiotics, such as gentamicin, noxythiolin and other antibiotics to prevent infection; prokinetic agents to promote bowel motility, agents to prevent collagen crosslinking such as cis-hydroxyproline and D-penicillamine; anti-cancer agents; neurotransmitters; hormones; immunological agents including elemetals and antibodies; nucleic acids including anti-sense agents; fertility drugs, psychoactive drugs; and local anesthetics, among numerous additional agents.

The methods and systems disclosed herein may also be utilized to deliver living cells to desired sites in a recipient. Examples of such cells include but are not limited to stem cells, bone marrow derived stem cells, adipose derived stem cells, bone marrow stromal cells, bone cells, hepatocytes, keratinocytes, chondrocytes, osteocytes, osteoblasts, osteoclasts, mesenchymal stem cells, fibroblasts, muscle cells, parenchymal cells, cells of intestinal origin, nerve cells, skin cells, endothelial cells, epithelial cells, and smooth muscle cells. These cells may be cultured, differentiated, or expanded prior to seeding. These cells may be concentrated prior to implantation by methods such as centrifugation or filtration. Thus, the medical implants seeded may function as adhesion substrates, anchoring cells to be transplanted to effect the survival, growth and ultimately, grafting and or anchoring of the transplanted cells to normal cellular tissue.

Other useful cell types may include bone marrow derived stem cells, adipose derived stem cells, bone marrow stromal cells, chondrocytes, osteocytes, osteoblasts, osteoclasts, mesenchymal stem cells, fibroblasts, muscle cells, hepatocytes, parenchymal cells, cells of intestinal origin, nerve cells, and skin cells, and may be provided as primary tissue explants, preparations of primary tissue explants, isolated cells, cell lines, trans formed cell lines, and host cells. The implants may also include additional components such as biologically active agents or factors that alter the characteristics, such as osteoinductivity, metabolic agents, resorbability, strength, adherence, injectability, and frictional characteristics.

Immune responses to cortical bone grafts and other substrates (e.g., cement, IPN, etc.) may be minimized while improving osteoinductive potential by modifying the grafts to have an osteoinductive surface that the recipients body will accept as its own tissue type and therefore will not reject it or otherwise cause to fail. Such a process provides for the osteoinductive surface modification to be achieved via seeding of the surface of a porous graft substrate with periosteal cells that have been previously harvested either from the graft recipient or from an allogenic or xenogenic donor source.

Porous substrates which may be used in connection with the disclosed methods and systems include allograft, xenograft, or other non-human animal-based materials such as collagen and other peptide comprising implants. Synthetic materials including ceramics, hydroxyapatite, bioresorbable polymers and the like may also be used as graft materials.

In certain embodiments, the pore size of the grafts may be configured to accommodate the dimensions of the biological components and cultured cells that are to be distributed or seeded into the grafts. The pore size may also be configured to accommodate the viscosity of aqueous compositions which are used to hydrate and/or reconstitute the grafts. The high viscosity of certain aqueous compositions may be due to the inclusion of proteins and other high molecular weight biomolecules. Thus, the consideration of scaffold pore size, density, and porosity may be configured to influence the behavior and quality of the regenerated tissue. The pore size for bone regeneration is preferably about 100 to about 600 microns.

Synthetic polymers useful for use in synthetic grafts include, but are not limited to: polyhydroxybutyrate (PHB); poly-n-vinyl pyrrolidone; polyorthoesters; polyanhydrides; polycyanoacrylates; polydepsipeptides; polydihydropyrans; poly-DL-lactide (PDLLA); polyesteramides; polyesters of oxalic acid; polyglycolide (PGA); polylactide-co-glycolide (DLPLG); polyetheretherketone (PEEK); polyetherketoneketone (PEKK); polyiminocarbonates; polylactides (PLA); polyorthoesters; poly-p-dioxanone (PDO); polypeptides; polyphosphazenes; polysaccharides; polyurethanes (PU); polyvinyl alcohol (PVA); poly-β-hydroxypropionate (PHPA); poly-β-hydroxybutyrate (PBA); poly-γ-valerolactone; poly-β-alkanoic acids; poly-β-malic acid (PMLA); poly-ε-caprolactone (PCL); and trimethylene carbonate (TMC), to name a few.

In some embodiments, the synthetic substrates may include polymers that are biostable, while in other embodiments, the synthetic substrates may include polymers that are bioresorbable. Suitable inorganic substrates may also include various types of natural and non-naturally occurring calcium phosphates, such as tricalcium phosphate, hydroxy apatite, poorly crystalline apatite calcium phosphate (PCA), amorphous calcium phosphate (ACP). As the main inorganic component of bone consists of a highly substituted calcium phosphate (CaP) apatite, synthetic bone substitutes comprising the various forms of CaP are particularly useful. Such CaP based materials include hydroxyapatite, carbonated apatite, fluoroapatite, alpha- and beta-tricalcium phosphate, tetracalcium phosphate, octacalcium phosphate, and combinations thereof. The materials are preferably configured to have an appropriate level of porosity, pore size, and size of the interconnections between pores.

It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

What is claimed is:

1. A container for storing a porous substrate comprising:
   an internal cavity maintained under negative pressure, the internal cavity comprising a receiving chamber configured to receive a biological solution and a storage chamber configured to store the porous substrate;
   a plurality of channels coupling the receiving chamber and the storage chamber;
   a septum coupled to the receiving chamber and disposed externally of the internal cavity, wherein the septum is resealable after puncture with a needle syringe to maintain the negative pressure in the internal cavity; and
   wherein the plurality of channels is configured to disperse the distribution of the biological solution along a longitudinal length of the porous substrate at substantially the same time once the receiving chamber receives the biological solution.

2. The container of claim 1, wherein the container comprises a seal adjacent a periphery of the internal cavity so as to reduce a volume of air space within the container.

3. The container of claim 1, further comprising one or more supporting members configured to elevate and support the container in a substantially stable position.

4. The container of claim 1, further comprising top, side and bottom walls defining an inner surface of the container.

5. The container of claim 4, wherein the bottom wall is angled downward from the plurality of channels.

6. The container of claim 4, wherein the container further comprises a lip surrounding a periphery of the container.

7. The container of claim 6, wherein the top wall is hermetically sealed to the lip adjacent the container periphery.

8. A container for storing a porous substrate comprising:
   an internal cavity maintained under negative pressure, the internal cavity comprising a receiving chamber configured to receive a biological solution, a storage chamber configured to store the porous substrate, and top, side and bottom walls defining an inner surface of the container; and
   a septum coupled to the receiving chamber and disposed externally of the internal cavity;
   a plurality of channels coupling the receiving chamber and the storage chamber, wherein the bottom wall is angled downward from the plurality of channels; and wherein the plurality of channels is configured to disperse the distribution of the biological solution along a longitudinal length of the porous substrate at substantially the same time once the receiving chamber receives the biological solution.

9. The container of claim 8, wherein the septum is resealable after puncture with a needle syringe to maintain the negative pressure in the internal cavity.

10. The container of claim 8, further comprising one or more supporting members configured to elevate and support the container in a substantially stable position.

11. The container of claim 8, wherein the container further comprises a lip surrounding a periphery of the container.

12. The container of claim 11, wherein the top wall is hermetically sealed to the lip adjacent the container periphery.

13. A container for storing a porous substrate comprising:

an internal cavity maintained under negative pressure, the internal cavity comprising a receiving chamber configured to receive a biological solution and a storage chamber configured to store the porous substrate;

a plurality of channels coupling the receiving chamber and the storage chamber;

a lip surrounding a periphery of the container, wherein the top wall is hermetically sealed to the lip adjacent the container periphery; and a septum coupled to the receiving chamber and disposed externally of the internal cavity, wherein the septum is resealable after puncture with a needle syringe to maintain the negative pressure in the internal cavity, wherein the plurality of channels is configured to disperse the distribution of the biological solution along a longitudinal length of the porous substrate at substantially the same time once the receiving chamber receives the biological solution.

14. The container of claim 13, wherein the bottom wall is angled downward from the plurality of channels.

15. The container of claim 13, further comprising one or more supporting members configured to elevate and support the container in a substantially stable position.

* * * * *